US009051554B2

(12) United States Patent
Varadaraj

(10) Patent No.: US 9,051,554 B2
(45) Date of Patent: Jun. 9, 2015

(54) HARVESTING ALGAE BY FOAM AGGREGATION AND FILTRATION

(71) Applicant: Ramesh Varadaraj, Flemington, NJ (US)

(72) Inventor: Ramesh Varadaraj, Flemington, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 17 days.

(21) Appl. No.: 14/055,102

(22) Filed: Oct. 16, 2013

(65) Prior Publication Data

US 2014/0141495 A1 May 22, 2014

Related U.S. Application Data

(60) Provisional application No. 61/727,827, filed on Nov. 19, 2012.

(51) Int. Cl.
*C12N 1/12* (2006.01)
*C12N 1/02* (2006.01)

(52) U.S. Cl.
CPC ... *C12N 1/12* (2013.01); *C12N 1/02* (2013.01)

(58) Field of Classification Search
None
See application file for complete search history.

(56) References Cited

U.S. PATENT DOCUMENTS

| 5,616,493 | A * | 4/1997 | Cahoon | 435/246 |
|---|---|---|---|---|
| 2008/0254529 | A1* | 10/2008 | Freeman | 435/257.1 |
| 2010/0184197 | A1* | 7/2010 | Dong et al. | 435/257.1 |
| 2010/0267122 | A1* | 10/2010 | Chinnasamy et al. | 435/257.3 |

FOREIGN PATENT DOCUMENTS

| JP | 2005261343 A | 9/2005 |
|---|---|---|
| WO | WO 9603494 A1 * | 2/1996 |
| WO | 9828082 A1 | 7/1998 |

OTHER PUBLICATIONS

Wong ("Miscellaneous Fresh Water Microalgae Identification Fremont Area" 1-4, available at msnucleus.org/watersheds/biological/microalgaegen.html, webcapture indicating publication in 2001 attached).*
Zhang, Sheng [Reprint Author],Liu, Yang, Zhang, Xiao-jian, Xie, Shu-guang, "Treating of algae-laden raw water with GAC-sand dual media deep bed dissolved air flotation/filtration", Huanjing Kexue, Sep. 30, 2004, vol. 25, No. 5, pp. 52-56. Dept Environm Sci and Technol, Tsing Hua Univ, Beijing, 100084, China.
Green, F. B., Bernstone, L., Lundquist, T. J., Muir, J.; Tresan, R. B., Oswald, W. J., "Methane fermentation, submerged gas collection, and the fate of carbon in advanced integrated wastewater pond systems", Water Science and Technology (1995), 31(12, Waste Stabilisation Ponds and the Reuse of Pond Effluents), 55-65, Elsevier.
Vosloo, P. B. V., Williams, P. G., Rademan, R. G., "Pilot and full-scale investigations on the use of combined dissolved-air flotation and filtration (DAFF) for water treatment", Water Pollution Control (Maidstone, England) (1986), 85(1), 114-21, Geustyn Forsyth and Joubert Inc., UK.

* cited by examiner

*Primary Examiner* — Jon P Weber
*Assistant Examiner* — Charles Zoltan Constantine
(74) *Attorney, Agent, or Firm* — David M. Weisberg

(57) ABSTRACT

Methods are provided for separating algae from an aqueous environment. An aqueous feed containing algae can be mixed in a turbulent manner in an aerated environment. The turbulent mixing can be sufficient to create a foam within the aqueous feed. The formation of the foam can also result in agglomeration of algae into larger size algae aggregates, which can then be filtered under pressure. Due to the larger size of the algae aggregates, the pressurized filtration can reduce/minimize the tendency to clog the filter, as the algae aggregates can generally be too large to fit within the pores of the filter. The filter can preferably be located at the bottom of the vessel holding the aqueous feed. This can assist in allowing the algae to remain in a cake above the filter, as opposed to having the algae dissolve back into the aqueous feed.

20 Claims, 1 Drawing Sheet

*Cyclotella* WT293 (ash free dry weight ≈ 600 mg/L; cells/mL ≈ 6x10⁶)

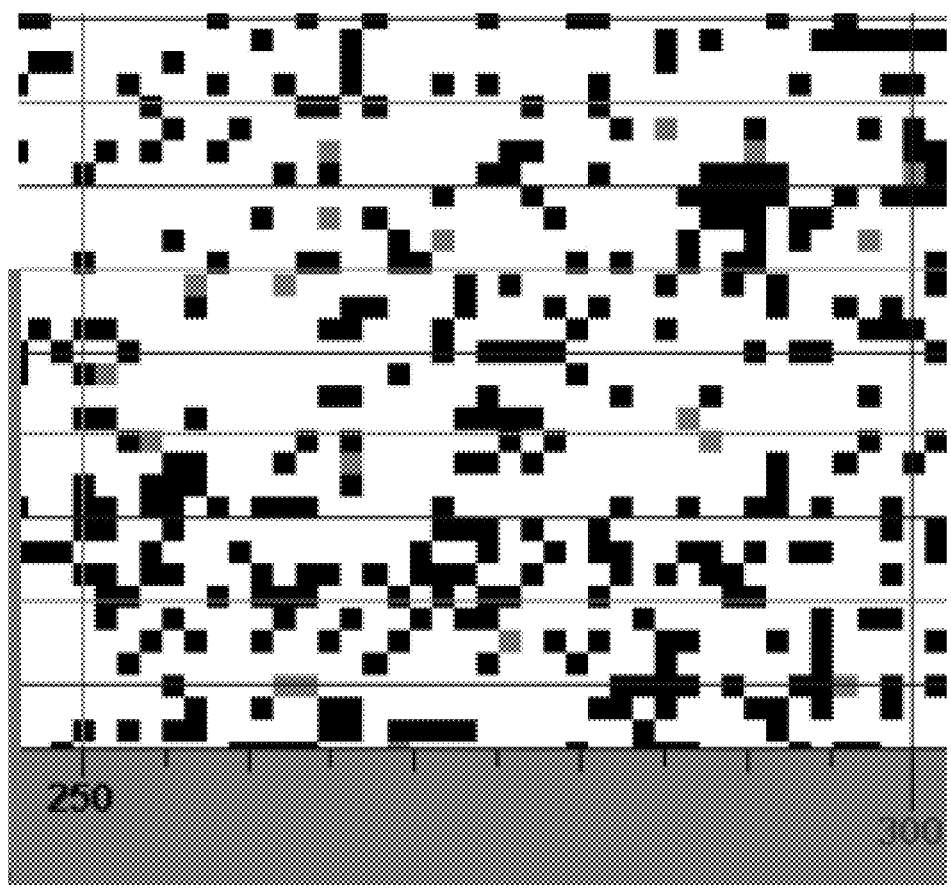
*Cyclotella* WT293 (ash free dry weight ≈ 600 mg/L; cells/mL ≈ 6x10$^6$)

HARVESTING ALGAE BY FOAM AGGREGATION AND FILTRATION

CROSS-REFERENCE TO RELATED APPLICATIONS

This application claims the benefit of U.S. Provisional Application Ser. No. 61/727,827 filed on Nov. 19, 2012; which is incorporated herein in its entirety by reference.

FIELD OF THE INVENTION

This invention relates to methods for harvesting algae from an aqueous environment.

BACKGROUND OF THE INVENTION

Developing renewable sources of feedstocks based on biomass for making distillate products, such as fuels or lubricants, is an area of ongoing interest. Use of biomass as a feedstock source can be attractive from a perspective of avoiding depletion of mineral oil and gas sources. However, a variety of challenges remain in developing technologies for harvesting and processing feeds derived from biomass.

One potential source of biomass-derived feedstocks is algae. Algae is an advantageous form of biomass in part because algae can be grown in artificially constructed ponds. Such algae growth ponds can be placed in desirable locations, such as locations that do not compete with production of food for human consumption. However, algae grown in a pond or other aqueous environment are typically present in a concentration corresponding to a few weight percent of the environment or less. Thus, one of the difficulties with using algae as a biomass source is the need to separate the relatively low concentration of algae from the water which is the majority component of the aqueous environment.

Some previous efforts to separate algae from an aqueous environment have used dissolved air flotation. In a conventional dissolved air flotation method, air is bubbled into an aqueous environment containing algae. The air is bubbled into the aqueous environment with the goal of having the algae attach to or agglomerate on the bubbles. As the bubbles reach the surface of the aqueous environment, algae becomes concentrated at the surface. The surface of the aqueous environment can then be skimmed to capture the algae at the surface. However, the skimming process tends to be inefficient, in part because algae that have traveled to the surface of the aqueous environment can fall back into the bulk portion of the environment. The algae that remain in the aqueous environment pose problems in part due to environmental regulations for the allowable concentration of species in waste water. Additionally, controlling the conditions in the aqueous environment is difficult, as the process is sensitive to small fluctuations within the environment.

Japanese Published Patent Application No. JP 2005261343 appears to describe a variation on dissolved air filtration. Based on the abstract, it appears that water is passed through a horizontal filter in an upward direction. Air bubbles are introduced from the bottom of the aqueous environment. The abstract describes the method as being useful for avoiding clogging of the filter.

SUMMARY OF THE INVENTION

In an embodiment, a method is provided for harvesting algae. The method can include mixing an aqueous feed containing algae under turbulent conditions in an aerated environment, the turbulent conditions being effective for formation of a foam; and filtering the aqueous feed through a filter medium at a pressure of about 25 psig (about 170 kPag) to about 1500 psig (about 10.3 MPag) to substantially separate the algae from the aqueous feed.

In another embodiment, a method is provided for harvesting algae. The method can include mixing an aqueous feed containing at least two types of algae under turbulent conditions in an aerated environment, the turbulent conditions being effective for formation of a foam, the algae comprising at least 10 wt % of each of the at least two types of algae relative to the total weight of algae in the feed; and filtering the aqueous feed through a filter medium at a pressure of about 25 psig (about 170 kPag) to about 1500 psig (about 10.3 MPag) to substantially separate the algae from the aqueous feed.

In still another embodiment, a method is provided for harvesting algae. The method can include mixing an aqueous feed containing algae under turbulent conditions in an aerated environment, the turbulent conditions being effective for formation of a foam, the algae comprising at least 10 wt % of a first type of algae relative to the total weight of algae in the feed, and at least 10 wt % of a second type of algae relative to the total weight of algae in the feed, the first type of algae having a first morphology and the second type of algae having a second morphology; and filtering the aqueous feed through a filter medium at a pressure of about 25 psig (about 170 kPag) to about 1500 psig (about 10.3 MPag) to substantially separate the algae from the aqueous feed.

BRIEF DESCRIPTION OF THE DRAWINGS

FIG. 1 shows a micrograph of algae and algae aggregates at a liquid/foam interface.

DETAILED DESCRIPTION OF THE EMBODIMENTS

In various embodiments, methods are provided for separating algae from an aqueous environment. An aqueous feed containing algae can be mixed in a turbulent manner in an aerated environment. The turbulent mixing can be sufficient to create a foam within the aqueous feed. The formation of the foam can also result in agglomeration of algae into larger size algae aggregates. The aqueous feed can then be filtered under pressure. Due to the larger size of the algae aggregates, the pressurized filtration can have a reduced/minimized tendency to clog the filter, as the algae aggregates can generally be too large to fit within the pores of the filter. The filter can preferably be located at the bottom of the vessel holding the aqueous feed. This can assist in allowing the algae to remain in a cake above the filter, as opposed to having the algae dissolve back into the aqueous feed. Optionally, the steps of turbulent mixing and filtration can be performed consecutively, which may involve transferring the turbulently mixed aqueous feed from a mixing vessel to a filtration vessel.

Algae Feedstock

In the discussion herein, a feed derived from a biological source (i.e., a biocomponent feed(stock)) refers to a feedstock derived from a biological raw material component, such as vegetable fats/oils or animal fats/oils, fish oils, pyrolysis oils, and algae lipids/oils, as well as components of such materials. In particular, a feed derived from a biological source can be a feed of algae in an aqueous environment, such as an algae culture or other feed containing algae in water.

Major classes of lipids can include, but are not necessarily limited to, fatty acids, glycerol-derived lipids (including fats, oils and phospholipids), sphingosine-derived lipids (including ceramides, cerebrosides, gangliosides, and sphingomyelins), steroids and their derivatives, terpenes and their derivatives, fat-soluble vitamins, certain aromatic compounds, and long-chain alcohols and waxes.

In living organisms, lipids generally serve as the basis for cell membranes and as a form of fuel storage. Lipids can also be found conjugated with proteins or carbohydrates, such as in the form of lipoproteins and lipopolysaccharides.

Algae oils or lipids can typically be contained in algae in the form of membrane components, storage products, and/or metabolites. Certain algal strains, particularly microalgae such as diatoms and cyanobacteria, can contain proportionally high levels of lipids. Algal sources for the algae oils can contain varying amounts, e.g., from 2 wt % to 40 wt %, of lipids based on total weight of the biomass itself. Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui,* and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Pichochlorum, Pseudoneochloris, Pseudostaurastrum, Platymonas, Pleurochrysis, Pleurococcus, Prototheca, Pseudochlorella, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella,* and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema,* and *Xenococcus* species.

Turbulent Mixing in Aerated Environment

In various aspects, algae aggregates are formed by mixing an aqueous algae feed under effective conditions for forming a foam. In order to form a foam, the mixing can be performed under turbulent conditions in an aerated environment.

Turbulent mixing conditions are in contrast to mixing conditions that would generate laminar type flows within the aqueous feed. The turbulent versus laminar character of the flows within a feed can be characterized based on a Reynolds number. The Reynolds number, Re, is generally defined as $$Re = \frac{\rho v L}{\mu} \qquad (1)$$

In Equation (1), $\rho$ represents the density of the fluid; v represents the velocity of an object relative to the fluid; L represents a characteristic length; and $\mu$ represents the dynamic viscosity of the fluid. The length chosen for the characteristic length can be dependent on the nature of the flow. For example, in a circular mixing vessel, the characteristic length can be related to the radius of the vessel. For flow in a pipe, the characteristic length can be related to the diameter of the pipe. In both of these situations, the velocity, v, can refer to the velocity of the fluid relative to the wall of the mixing vessel or pipe.

Typically, a Reynolds number for a fluid of about 2500 or less, such as 2000 or less, can indicate a fluid undergoing laminar flow. Mixing under laminar flow conditions typically does not result in foam formation. By contrast, mixing conditions that add enough energy to a fluid to generate turbulent flow are expected to result in at least some foam formation. Turbulent flows generally correspond to a Reynolds number of at least about 4000, such as at least about 4500 or at least about 5000.

Any convenient method for generating a turbulent flow can be used. Preferably, the method allows for a low energy of mixing to achieve the turbulent flow. A paddle mixer can be one option for introducing mixing energy into the aqueous algae feed. A paddle speed of about 100 rpm, for example, can be sufficient to generate a turbulent flow. Another option can be to introduce the feed into a vessel by directing a flow of the feed on to a surface.

The Reynolds number corresponding to effective mixing for generating sufficient turbulent flow can be dependent on the type of algae in the aqueous algae feed. Some types of algae facilitate foam formation, and therefore a foam can form at relatively lower Reynolds number conditions. Another way to reduce the required Reynolds number can be to add a separate agent that facilitates foam formation. For example, many soap-like or detergent-like compounds can facilitate the formation of foam in an aqueous environment. The use of a separate foaming agent is optional, and is not generally preferred. If a foaming agent is used, any convenient surfactant compound can be used, such as a carageenan compound, a compound with a long carbon chain with a phosphate or sulfate tail, or another anionic, cationic, or non-ionic surfactant. The concentration of the foaming agent, when used, can be comparable to the concentration of algae in the aqueous environment. In various embodiments, the optional foaming agent can have a concentration of about 1 wt % or less relative to the weight of the algae feed, such as about 0.5 wt % or less and/or at least about 0.25 wt %.

In addition to performing turbulent mixing, the mixing can preferably be performed in an aerated environment. Formation of a foam typically requires incorporation of a gas from the environment, as the individual bubbles in the foam should contain a gas that balances the pressure on the walls of the bubble. Air can be a convenient and low cost option for providing an aeration gas, but other gases such as nitrogen could also be used. The aqueous environment can be aerated by any convenient method. If the turbulent mixing is performed separately from filtration, aeration can be provided by maintaining a head space of a suitable aeration gas above the aqueous algae feed. Additionally or alternately, air (or another aeration gas) can be bubbled through the algae feed. If the mixing is performed concurrently with filtration, the aeration gas can be used to pressuring the filtration and mixing vessel, and/or an aeration gas can be bubbled into the feed.

The temperature of the algae feed during turbulent mixing can be approximately ambient or room temperature, such as from about 10° C. to about 40° C. Cooler temperatures still above the freezing point of water could also be acceptable, but are not generally preferred. Temperatures of about 35° C. to about 40° C. are also acceptable, but these temperatures and higher can be sufficient to return algae in algae aggregates to an individual state. The pressure during turbulent mixing can be any convenient pressure. If the mixing is performed in the same vessel as the filtration, the filtration pressure can be used during mixing.

Formation of Algae Aggregates

Conventional filtration of an algae feed tends to result in poor performance. This can be due in part to clogging of the channels or pores in the filter medium. This can additionally or alternately be due in part to formation of a filter cake on the surface of the filtration medium that has low permeability for water.

In order to improve filtration performance, the algae in an algae feed can be aggregated to form algae aggregates. Formation of foam in the aqueous algae feed can allow algae within the feed to form aggregates. Instead of the algae behaving like individual particles, aggregation can cause the algae to behave according to the larger size of the aggregated algae. Individual algae can have a variety of sizes, depending on the type of algae. The size of individual algae can range from about 0.5 μm to about 10 μm. By forming algae aggregates, the characteristic size for the algae can be increased. The increased aggregate size of the algae aggregates can reduce the tendency of the algae to clog the pores of the filter medium. Similarly, the larger aggregate size can also reduce the tendency of the algae to form a filter cake with a low permeability.

The increased size of the algae aggregates can also improve filtration rates based on another factor. The packing density for particles with a regular shape can typically be invariant with the radius (or other characteristic length) for the particles. For example, the density of hard spherical particles can depend on the type of packing arrangement, but the density is not typically dependent on the radius of the spheres, so long as all of the spheres have approximately the same size. However, the way the volume between particles is distributed can generally vary with size. For a close packed arrangement of spheres, the size of the gaps or channels between the spheres can typically increase as the radius of the spheres increases.

During filtration of algae from an aqueous environment, the algae can accumulate in a filter cake on the retentate side of the filter medium. During filtration, the material that accumulates in the filter cake can add to the pressure drop required to pass liquid through the filter. For particles with larger particle sizes, the gaps or channels in the filter cake can be larger, which can reduce the pressure drop required to pass liquid through the filter cake. By forming algae aggregates, the average "particle" size in the algae feed can be increased from the algae size to the algae aggregate size. Based on this increase in effective particle size, formation of algae aggregates can reduce the pressure drop required to pass water through the filter cake during filtration.

In addition to increasing the average particle size, forming algae aggregates can also change the morphology of the "particles" in the algae feed. For example, individual algae can have various shapes, such as spherical, cylindrical, or disc-like. When the individual algae are aggregated, however, the shape of the aggregated algae may not match the morphology of the individual algae. The shape and size of the aggregates formed from algae can be dependent on the nature of the algae, including the surface properties (such as roughness) for the algae. For example, an algae type with individual algae of a spherical morphology may form aggregates of an irregular shape. Any type of irregular shape can have a reduced packing density that can improve the flow properties through a filter cake formed during filtration.

Still another option for improving the flow properties through a filter cake can be to use an algae feed with more than one type of algae. Having multiple types of algae, such as at least two types of algae, can provide a filter cake with improved filtration properties for a variety of reasons. First, for particles of different shapes, the presence of multiple shapes can tend to reduce potential packing density. Preferably, the characteristic lengths of the algae can be sufficiently similar so that the algae with smaller characteristic lengths do not occupy void spaces within an aggregate of the algae with larger characteristic lengths.

One option can be to use a mixture of algae types, such as at least two types of algae, so that a first type of algae with beneficial properties for aggregation and/or packing density can be combined with a second type of algae with other desirable properties but poor aggregation and/or poor properties in a filter cake. For example, an algae with good aggregation properties can be mixed with an algae that is efficient for production of desirable product molecules.

In various aspects, algae feeds containing more than one type of algae can comprise at least 10 wt % of a first type (such as species or strain) of algae, relative to the total weight of algae in the feed, and at least 10 wt % of a second type of algae. Due to the relatively low concentration of algae in many algae feeds, it is noted that the total weight percent of all algae in a feed can typically be less than 10 wt % relative to the weight of the feed. In one embodiment, the weight percentage of the first type of algae can be greater than the second type of algae. The ratio of the first type of algae to the second type of algae can be at least 1:1, e.g., at least 1.5:1, at least 2:1, or at least 3:1. Additionally or alternately, the ratio of the first type of algae to the second type of algae can be 9:1 or less, e.g., 6:1 or less, 5:1 or less, or 4:1 or less.

In still other aspects, more than two types of algae may be included in the algae feed. In general, an algae feed can contain any number of algae types. However, algae types that are present as less than about 10 wt % of the total algae content are not believed to have a substantial impact on the resulting aggregate structures. Of course, a blend of various types of algae can also be viewed as a single "mixed" type of algae for the purposes of characterizing the performance of the feed during filtration.

When an algae feed contains a mixture of two or more types of algae, the morphology of each type of algae can be any convenient morphology. Examples of morphology for algae can include, but are not necessarily limited to, spherical, cylindrical, disc-like, and irregular. It is noted that a spherical morphology, for example, need not be perfectly spherical and may be only approximately spherical. Preferably, at least two of the algae types in the mixture can have different morphologies. For spherical or disc-like morphology, a characteristic dimension for an algae can be a diameter. For a cylindrical morphology, a characteristic dimension for an algae can be a length. Preferably, a ratio of characteristic dimensions for a first type of algae and a second type of algae can be from about 1:3 to about 3:1, such as less than 2:1 and/or at least 1:2.

Filtration of Aqueous Feed Containing Aggregated Algae

Filtration of the aqueous feed to separate the aggregated algae from water can be performed continuously, such as by performing filtration in the same vessel as the turbulent mixing while the mixing is occurring. Alternatively, the filtration can be performed after algae aggregation.

When filtration is performed after algae aggregation, the feed containing aggregated algae can be aged for a period of time prior to filtration. The aging period can be any convenient amount of time that is short enough so that the algae feed is still substantially aggregated during filtration. The amount of aging between aggregate formation and filtration can be from about 30 seconds to about an hour, e.g., at least one minute, a half an hour or less, and/or 20 minutes or less.

During filtration, the temperature can be maintained near ambient temperature, such as from about 10° C. to about 40° C. As noted above, higher temperature can have a tendency to separate aggregated algae. The pressure during filtration can be a pressure that facilitates transporting water through the filter medium.

The pressure can preferably be selected to provide a sufficient pressure differential for filtration at a commercially desirable speed. Depending on the embodiment, pressures from about 25 psig (about 170 kPag) to about 1500 psig (about 10.3 MPag) can be suitable, e.g., at least about 40 psig (about 280 kPag), at least about 100 psig (about 690 kPag), about 1000 psig (about 6.9 MPag) or less, and/or about 600 psig (about 4.1 MPag) or less.

During filtration, the algae feed can be filtered through the filter medium in a direction roughly aligned with gravity, such as a direction that differs from the direction of gravitational pull by about 45° or less. This can reduce/minimize the tendency for the algae in the filter cake to re-enter the aqueous feed on the retentate side.

The filter medium can be any convenient type of membrane, filter, or other porous material suitable for performing filtration. The pore size of the filter medium can be about 20 μm or less, e.g., about 10 μm or less, about 5 μm or less, or about 3 μm or less. Preferably, the pore size of the filter medium can be at least about 1 μm in order to facilitate appropriately high filtration rates.

Using filtration to separate algae from the aqueous environment as filtration is believed to be a reliable method for reducing the algae content of the permeate to a sufficiently low level to meet typical standards for purified wastewater. As a result, the need for further processing of the permeate water prior to disposal can be reduced/minimized/eliminated.

ADDITIONAL EMBODIMENTS

Embodiment 1

A method for harvesting algae, comprising: mixing an aqueous feed containing algae under turbulent conditions in an aerated environment, the turbulent conditions being effective for formation of a foam; and filtering the aqueous feed through a filter medium at a pressure of about 25 psig (about 170 kPag) to about 1500 psig (about 10.3 MPag) to substantially separate the algae from the aqueous feed.

Embodiment 2

The method of Embodiment 1, wherein the algae separated from the aqueous feed comprise algae aggregates.

Embodiment 3

The method of Embodiment 2, wherein the algae have a first morphology and the algae aggregates have a second morphology.

Embodiment 4

A method for harvesting algae, comprising: mixing an aqueous feed containing at least two types of algae under turbulent conditions in an aerated environment, the turbulent conditions being effective for formation of a foam, the algae comprising at least 10 wt % of each of the at least two types of algae relative to the total weight of algae in the feed; and filtering the aqueous feed through a filter medium at a pressure of about 25 psig (about 170 kPag) to about 1500 psig (about 10.3 MPag) to substantially separate the algae from the aqueous feed.

Embodiment 5

The method of any of the above embodiments, wherein a first type of algae has a first morphology and a second type of algae has a second morphology.

Embodiment 6

The method of Embodiment 5, wherein the first type of algae has a cylindrical morphology and the second type of algae has a spherical morphology.

Embodiment 7

The method of Embodiments 5 or 6, wherein the separated algae comprise algae aggregates, and wherein the algae aggregates have a morphology different from the morphology for the first type of algae and different from the morphology for the second type of algae.

Embodiment 8

The method of Embodiments 5 to 7, wherein a ratio of a characteristic length of the first type of algae and a characteristic length of a second type of algae is from about 1:3 to about 3:1.

Embodiment 9

The method of any of the above embodiments, further comprising: aging the aqueous feed containing algae after mixing and prior to filtering for about 5 minutes to 24 hours.

Embodiment 10

The method of any of the above embodiments, wherein the mixing and filtering are performed concurrently.

Embodiment 11

The method of any of the above embodiments, wherein the mixing and filtering are performed in the same vessel.

Embodiment 12

The method of any of the above embodiments, wherein the filtration medium has a pore size of from about 1 μm to about 20 μm.

Embodiment 13

The method of any of the above embodiments, further comprising adding about 0.25 wt % to about 1 wt % of a foaming agent to the algae feed.

Embodiment 14

The method of any of the above embodiments, wherein the Reynolds number of the algae feed during mixing is at least about 4000.

Example 1

Detection of Algae Aggregates (*Cyclotella*)

A ~50 ml culture of *Cyclotella* WT 293 was placed in a ~100 mL glass container. The container was capped and the sample was vigorously hand shaken for about 5 minutes to create visible foam. A laser reflectance microscope was placed into the sample and micrographs were taken at various locations. Micrographs were taken at the top of the foam, in the body of the foam, and the interface of the liquid in equilibrium with the foam.

A representative micrograph of algae aggregates detected at the liquid/foam interface is shown in FIG. 1. The micrograph in FIG. 1 has an expanded scale of from 250 to 300 microns, meaning that the scale covers ~50 microns. In the micrograph, individual *Cyclotella* are imaged as black squares of ~4-5 micron size. This roughly corresponds to the 4 to 5 micron characteristic length of the individual *Cyclotella* algae. The individual *Cyclotella* algae have a roughly cylindrical morphology. Aggregates of *Cyclotella* are represented as "aggregates of square blocks". FIG. 1 clearly shows the presence of aggregates at the liquid/foam interface.

FIG. 1 is representative of the aggregates observed at all three locations scanned with the micrograph. For comparison, micrographs were also obtained at the liquid surface of a *Cyclotella* algae sample that was prepared as described above, but that was not shaken in order to generate a foam. No aggregates were observed in the algae sample in the absence of a foam.

Example 2

Filtration of Aggregated *Cyclotella* Sample

The *Cyclotella* sample in Example 1 that was shaken in order to form algae aggregates was then filtered. The ~50 mL sample with aggregated *Cyclotella* from Example 1 was immediately transferred to a constant pressure filtration apparatus. Filtration was conducted at ambient temperature (about 20-25° C.) and ~500 psig (~3.4 MPag) of pressure using a ~2.7 micron pore size filter paper. The permeate passed down through the filter paper in roughly the direction of gravitational pull. In a period of about 55 minutes, the ~50 ml of the sample from Example 1 was filtered through the filter paper. The harvested *Cyclotella* was recovered from the filter paper as a filter cake on the retentate side of the filter.

Comparative Example 3

Non-Aggregated *Cyclotella*

As a comparison, a control experiment was conducted. A ~50 ml sample of *Cyclotella* in water was prepared. The sample was not shaken according to the method of Example 1. The non-aggregated *Cyclotella* sample was then placed in the filtering apparatus described in Example 2 in an attempt to filter the non-aggregated sample. After ~60 minutes, no filtrate was obtained.

The filter paper from this Comparative Example was examined under a light microscope. The ~2.7 micron pores of the filter paper were completely plugged with the *Cyclotella*, which is believed to be the cause of the lack of filtration. By contrast, the filter paper from Example 2 was also examined under a light microscope. The retentate from the filtration in Example 2 showed granular *Cyclotella*, but only a limited amount of clogging of the pores of the filter paper.

Example 4

Aggregation and Filtration of *Nannochloropsis*

The procedures of Examples 1 and 2 were used to also study a ~50 mL sample of foam aggregated *Nannochloropsis* WT 35 algae. The *Nannochloropsis* have a roughly spherical morphology with a characteristic length (diameter) of about 1 μm. After shaking the sample to form the foam and the aggregated algae, the *Nannochloropsis* sample was immediately transferred to a constant pressure filtration apparatus. Filtration was conducted at room temperature (about 20-25° C.) and a pressure of ~500 psig (~3.4 MPag) using a ~2.7 micron pore size filter paper. The 50 ml of the sample was passed through the filter paper in a period of about 2 minutes. The resulting retentate filter cake of *Nannochloropsis* was harvested from the filter paper.

It is noted that the aggregated *Nannochloropsis* sample has a faster filtration rate than the aggregated *Cyclotella* sample. Although the *Nannochloropsis* is smaller, it is believed that the aggregated *Nannochloropsis* contains aggregates that have a lower likelihood of clogging the pores of a filter medium and/or provide a more porous filter cake.

Comparative Example 5

Non-Aggregated *Nannochloropsis*

As a comparison, a control experiment was conducted using a ~50 mL sample of *Nannochloropsis* with formation of a foam to aggregate the algae. The algae culture was then filtered in the constant pressure filtration apparatus at ~500 psig (~3.4 MPag). After 60 minutes, only ~4.5 ml of filtrate was obtained from the permeate side of the filter.

What is claimed is:

1. A method for harvesting algae, comprising:
    mixing an aqueous feed containing algae under turbulent conditions in an aerated environment, the turbulent conditions being effective for formation of a foam, the foam having a liquid-foam interface; and
    filtering the aqueous feed through a filter medium at a pressure of about 25 psig (about 170 kPag) to about 1500 psig (about 10.3 MPag) to substantially separate the algae from the aqueous feed,
    wherein the aqueous feed containing algae is aged after mixing and prior to filtering for about an hour or less.

2. The method of claim 1, wherein the aqueous feed containing algae is aged after mixing and prior to filtering for at least about 5 minutes.

3. The method of claim 1, wherein the mixing and filtering are performed concurrently.

4. The method of claim 3, wherein the mixing and filtering are performed in the same vessel.

5. The method of claim 1, wherein the filtration medium has a pore size of from about 1 μm to about 20 μm.

6. The method of claim 1, further comprising adding about 0.25 wt % to about 1 wt % of a foaming agent to the algae feed.

7. The method of claim 1, wherein the Reynolds number of the algae feed during mixing is at least about 4000.

8. The method of claim 1, wherein the algae separated from the aqueous feed comprise algae aggregates.

9. The method of claim 8, wherein the algae have a first morphology and the algae aggregates have a second morphology.

10. A method for harvesting algae, comprising:
mixing an aqueous feed containing at least two types of algae under turbulent conditions in an aerated environment, the turbulent conditions being effective for formation of a foam, the foam having a liquid-foam interface, the algae comprising at least 10 wt % of each of the at least two types of algae relative to the total weight of algae in the feed; and
filtering the aqueous feed through a filter medium at a pressure of about 25 psig (about 170 kPag) to about 1500 psig (about 10.3 MPag) to substantially separate the algae from the aqueous feed,
wherein the aqueous feed containing algae is aged after mixing and prior to filtering for about an hour or less.

11. The method of claim 10, wherein the first type of algae has a cylindrical morphology and the second type of algae has a spherical morphology.

12. The method of claim 11, wherein the algae aggregates have a morphology different from the morphology for the first type of algae and different from the morphology for the second type of algae.

13. The method of claim 10, wherein a ratio of a characteristic length of a first type of algae and a characteristic length of a second type of algae is from about 1:3 to about 3:1.

14. The method of claim 10, wherein the aqueous feed containing algae is aged after mixing and prior to filtering for at least about 5 minutes.

15. The method of claim 10, wherein the mixing and filtering are performed concurrently.

16. The method of claim 15, wherein the mixing and filtering are performed in the same vessel.

17. A method for harvesting algae, comprising:
mixing an aqueous feed containing algae under turbulent conditions in an aerated environment, the turbulent conditions being effective for formation of a foam, the foam having a liquid-foam interface, the algae comprising at least 10 wt % of a first type of algae relative to the total weight of algae in the feed, and at least 10 wt % of a second type of algae relative to the total weight of algae in the feed, the first type of algae having a first morphology and the second type of algae having a second morphology; and
filtering the aqueous feed through a filter medium at a pressure of about 25 psig (about 170 kPag) to about 1500 psig (about 10.3 MPag) to substantially separate the algae from the aqueous feed,
wherein the algae aggregates have a morphology different from the morphology for the first type of algae and different from the morphology for the second type of algae.

18. The method of claim 17, wherein the first type of algae has a cylindrical morphology and the second type of algae has a spherical morphology.

19. The method of claim 17, wherein a ratio of a characteristic length of the first type of algae and a characteristic length of the second type of algae is from about 1:3 to about 3:1.

20. The method of claim 17, wherein the Reynolds number of the algae feed during mixing is at least about 4000.

* * * * *